(12) United States Patent
Lombardi et al.

(10) Patent No.: US 6,177,093 B1
(45) Date of Patent: Jan. 23, 2001

(54) METHOD AND SYSTEM FOR COLOR CUSTOMIZING COSMETIC MASS PRODUCTS

(75) Inventors: Jack Lombardi, Massapequa; Nicholas Morante, Selden, both of NY (US)

(73) Assignee: Color Access, Inc., Melville, NY (US)

( * ) Notice: Under 35 U.S.C. 154(b), the term of this patent shall be extended for 0 days.

(21) Appl. No.: 09/270,458

(22) Filed: Mar. 17, 1999

(51) Int. Cl.$^7$ .............................. A61K 6/00; A61K 7/00; A61K 7/021; A61K 7/025
(52) U.S. Cl. ............................... 424/401; 424/63; 424/64
(58) Field of Search ............................. 424/61, 69, 64, 424/63, 401

(56) References Cited

U.S. PATENT DOCUMENTS

| | | | |
|---|---|---|---|
| 4,705,083 | 11/1987 | Rossetti | 141/104 |
| 4,871,262 | 10/1989 | Krauss et al. | 366/160 |
| 4,967,938 | 11/1990 | Hellenberg | 222/144 |
| 4,977,522 | 12/1990 | David | 364/526 |
| 5,003,500 | 3/1991 | Gerber | 364/526 |
| 5,078,302 | 1/1992 | Hellenberg | 222/144 |
| 5,163,010 | 11/1992 | Klein et al. | 364/479 |
| 5,622,692 | 4/1997 | Rigg et al. | 424/63 |
| 5,780,018 * | 7/1998 | Collins et al. | 424/64 |
| 5,785,960 | 7/1998 | Rigg et al. | 424/63 |
| 5,945,112 | 8/1999 | Flynn et al. | 424/401 |

OTHER PUBLICATIONS

John A. Wenninger, & G.N. McEwen, Jr., Eds.;"International Cosmetic Ingredient Handbook—vol. 2" published by The Cosmetic, Toiletry, and Fragance Association, (7$^{th}$ ed. 1997).

Brochure entitled "Precise Color Communication—Color Control From Feeling to Instrumentation", by Minolta.

* cited by examiner

Primary Examiner—Thurman K. Page
Assistant Examiner—S. Howard
(74) Attorney, Agent, or Firm—Pennie & Edmonds LLP (57) ABSTRACT

The present invention relates to a method and system for creating a customized color cosmetic mass at the point of sale to a customer. The method includes selecting a final color, identifying a combination of pellets to create the final color upon combination thereof, heating the combination of pellets in a container to a specified temperature to form a heated mixture, transferring the heated mixture from the container to a mold, cooling the mold until the heated mixture solidifies to form the cosmetic mass, and disassembling the mold to release the mass. The system includes a plurality of pellets having at least two different colors, a programmable device for identifying a combination of pellets to provide a final color, a container for receiving the combination of pellets, a heating unit for heating the pellets to form a homogeneous heated mixture, a mold defining the shape of the cosmetic mass for receiving the homogeneous heated mixture, and a cooling unit for cooling the mold until the heated mixture solidifies into the cosmetic mass.

20 Claims, 4 Drawing Sheets

METHOD AND SYSTEM FOR COLOR CUSTOMIZING COSMETIC MASS PRODUCTS

FIELD OF THE INVENTION

The present invention concerns a method for color customizing lipstick and other cosmetic mass products at the point of sale to a customer.

BACKGROUND OF THE INVENTION

Customers of cosmetic products are often interested in selecting an optimum color shade for their cosmetics. As a result, cosmetic manufacturers often produce cosmetic products in a large variety of colors with the expectation of meeting a majority of customers needs. While manufacturers attempt to manufacture a large variety of colors, there are limits to the number of choices available. Manufacturers are cognizant of limited storage space and the desire to avoid waste which may be associated with colors which are found to be less popular. Selection of optimum color may also be hindered by stock availability. More popular color selections may be out of stock and today's "on-demand" consumers will often be unwilling to wait for their color choice to become available before switching to another brand. As a result, customized color selection has been developed in order to address a greater number of consumer's needs.

Customers may desire a particular color shade for any number of reasons. They may want to match a particular foundation, powder, or blush to their unique skin tone, or a particular lipstick to a garment or nail polish color. Alternatively, customers may want to match their foundation, lipstick, or other cosmetic product to their skin tone with a slightly darker or lighter, but complimentary, shade, or may be interested in matching their cosmetic product to a particular hair color or other color.

Several cosmetic manufacturers have been providing customers with flexibility in color choice for such articles as foundation and powders. For instance, Clinique and Clarion have installed computers at sales counters for the customer. Information concerning such factors as color shade, skin type, and other properties are input into the computer, which then determines the company's most closely matching product.

Other companies have provided custom blended foundations and powders. One company, Prescriptives, manually evaluates a subject's skin color and then the sales person attempts to adjust existing finished foundations and powders to match the evaluated subject's skin color. This method may be time consuming and may require extensive training of sales personnel.

One company, Trish McEvoy, provides customized lip coloring to the customer at the point of sale. In the Trish McEvoy custom pallette system, when a customer is unable to find an optimum color from the commercially available lipstick products, but desires something similar to a commercially available color, the customer selects the two most closely colored commercially available lipstick products. Then a portion of the lipstick mass from each color is cut off and manually placed into a square pallette. This pallette is then heated. During heating, the sales person mixes the material in the pallette by manually stirring it. Upon hardening in the pallette, the customer utilizes a brush to transfer the lipstick material from the pallette to the lips.

Several patents teach an apparatus or method for blending customized cosmetic products at the point of sale. For instance, U.S. Pat. No. 4,871,262 to Krauss et al. describes an automatic cosmetic dispensing system and method for blending selected cosmetic additives into a cosmetic cream base. The cosmetic additives are pumped from storage bottles into ajar containing the cream base. The mixture is stirred by a mixing rod, removed from the dispensing unit, sealed, and provided to the customer.

U.S. Pat. No. 5,622,692 to Rigg et al., the disclosure of which is incorporated herein by reference in its entirety, describes a method and apparatus for providing a customized skin foundation product. A skin analyzer is utilized for reading skin properties. A programmable device receives the reading from the skin analyzer and correlates an optimal formula from a preprogrammed set of formulas, and a formulation machine prepares the foundation product from various cosmetic chemical compositions. The formulation machine receives instructions from the programmable device in identifying the optimal formula. The optimal formula may be altered by customer input and manual alteration. U.S. Pat. No. 5,785,960 to Rigg et al. describes a method and apparatus similar to that described in U.S. Pat. No. 5,622,692 and further describes the use of a telemodem to utilize the method and apparatus at a remote location from a central location where the product is prepared.

Previous customization systems, such as those utilized for foundations, suffer from numerous problems. These systems frequently require a precise measurement of very small quantities of materials in order to match the formula generated by the computer algorithm. They utilize a large static mass of materials, which must be kept at the place of preparation. They require continuous dispensing, usually via pumps or nozzles, from the same masses of material in the course of preparation of multiple different foundations. The repeated dispensing results in an increased potential for contamination of the starting materials, and therefore, can result in a substantial waste of materials. The precision required in measuring out the particular raw materials also results in a poorer likelihood of accurate reproducibility of the same color without the use of highly trained personnel.

The present invention avoids these problems and provides a technique for creating color customized cosmetic mass products, such as lipstick and stick foundations. The starting materials are individual small units, dispensed only once, resulting in very little waste. Unlike the prior systems which relied on combinations of already available lipsticks, it is not even necessary to keep a lipstick inventory on hand. As a result, there will ultimately be fewer returns, and less wasted components, i.e., lipstick cases and packaging, for shades that become unpopular. The present invention also readily accommodates a change in customer shade preferences. Measurement is simple but very precise, resulting in reproducible colors. Also, the individual starting components are small, and relatively easily stored behind the counter. These and other benefits will be readily evident from the following discussion.

There is, therefore, a need for an improved lipstick customization process which can be readily utilized at the cosmetic counter, or similar point of sale location, to provide customized lipsticks. Other types of cosmetic mass products, such as cheek color cosmetics, stick foundations, or other similar color cosmetics, would also be producible with an improved customization technique.

SUMMARY OF THE INVENTION

Accordingly, the present invention is directed to a method and a system for creating a customized color cosmetic mass at the point of sale to a customer from a plurality of pellets having a plurality of colors. The method includes selecting a final color and identifying a combination of pellets from the plurality of pellets based upon a pellet weight and the pellet color to create the final color when the pellets are combined. The combination of pellets is then heated in a container to form a heated material. The heated material is transferred from the container to a mold having at least one opening defined therein defining the shape of at least one cosmetic mass. The mold is then cooled until the heated material solidifies into at least one cosmetic mass. The mold may then be disassembled to release the at least one cosmetic mass from the mold.

The step of selecting a final color may include selecting a final color from a standard color pallette. This embodiment may also include modifying the final color based upon customer input and repeating the modifying step until the modified final color is selected as the final color. In another embodiment, the step of selecting a final color includes reading an unknown color and comparing the unknown color to the standard color pallette to select a matching color as said final color. This method may also include displaying the matching color and the unknown color on a display unit. This embodiment may further include modifying the matching color based upon customer input. The displaying and modifying steps may be repeated until the matching color is selected as the final color.

The method may also include receiving a digital image of the customer, displaying the matching color on the digital image of the customer on a display unit, and modifying the matching color based upon customer input and repeating the displaying and modifying steps until the matching color is selected as the final color.

In another embodiment, the step of selecting a final color may include receiving a digital image of the customer and displaying the final color on the digital image of the customer on a display unit. In this embodiment, the step may also include reading an unknown color and comparing the unknown color to the standard color pallette to select a matching color. The matching color is preferably displayed with the unknown color on the digital image of the customer and the matching color may be modified based upon customer input. The displaying and modifying steps may be repeated until the matching color is selected as the final color.

The method may also include positioning the cosmetic mass in a dispensing unit. In one embodiment, the mixture is preferably stirred during heating to facilitate the formation of a heated mixture which is homogeneous. The method may further include storing the final color in a database.

The system of the present invention preferably includes a plurality of pellets having at least two different colors and a programmable device for identifying a combination of pellets based upon a weight and a color combination of the plurality of pellets so that when the combination of pellets is formed into a homogeneous mass, the combination of pellets provides a final color for the cosmetic mass. The system also includes a container for receiving the combination of pellets, a heating unit, a mold, and a cooling unit. The heating unit is for heating the combination of pellets in the container to form a homogeneous heated mixture. The mold may include at least one mold cavity for defining the shape of the cosmetic mass and for receiving the homogeneous heated mixture. The cooling unit may be used to cool the heated mixture in the mold until the heated mixture solidifies.

The cosmetic mass may be a lipstick, foundation, or blush. In one embodiment, the plurality of pellets preferably include at least one colorant selected from the group consisting of metal oxides, titanium dioxides, FD&C organic colors, D&C organic colors, natural pigments, and pearls.

In another embodiment, the heating unit is a block heater and the cooling unit is a cooling plate. A stirrer is provided for stirring the combination of pellets in the container to create the homogeneous heated mixture. The mold is preferably disassemblable to release the cosmetic mass therefrom.

The programmable device of the system may include a first input unit and is programmed to store a standard color pallette. The first input unit samples an unknown color and the programmable device compares the unknown color to the standard color pallette to identify a matching color. A second input device is preferably provided for receiving input from a customer to either select the matching color as the final color or to modify the matching color to provide the final color. A digital camera may be provided for generating a digital image for input to the programmable device. The programmable device is preferably programmed to receive the digital image, to manipulate the digital image, and to display the digital image in combination with the final color.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
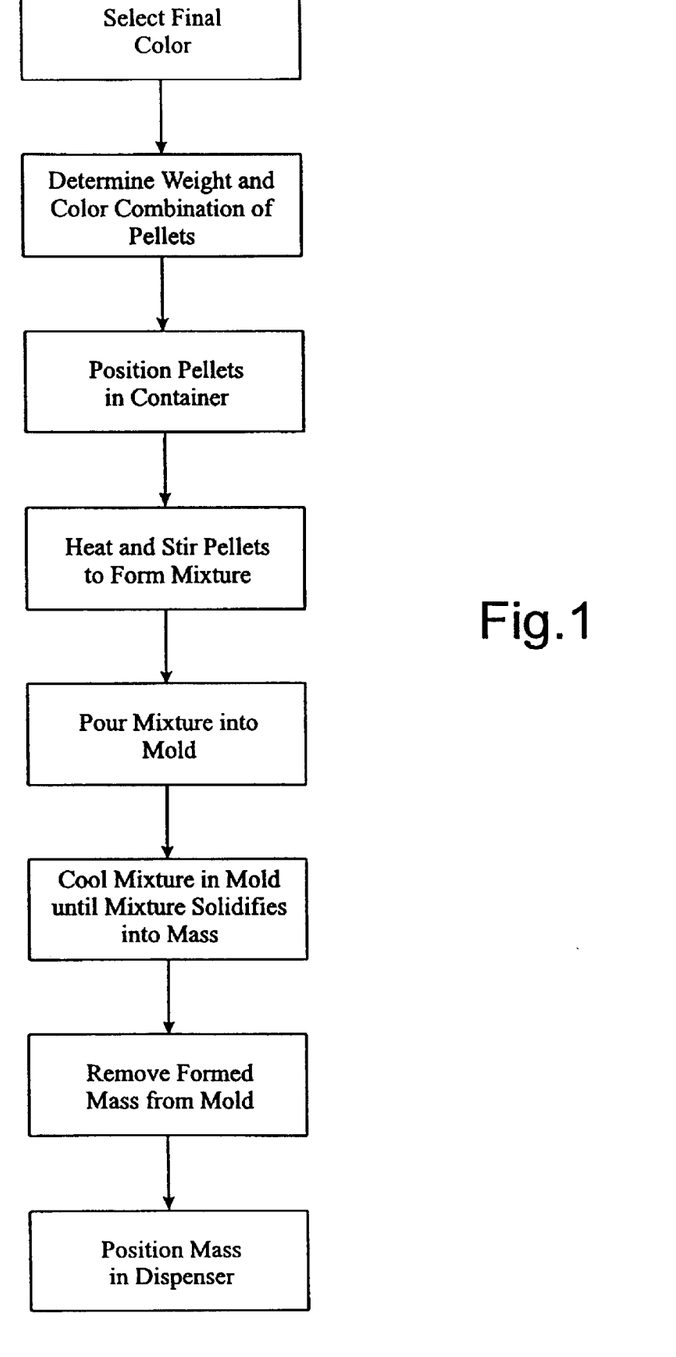
FIG. 1 is a diagram illustrating the method for providing a customized color cosmetic mass product of the present invention.
Figure 2:
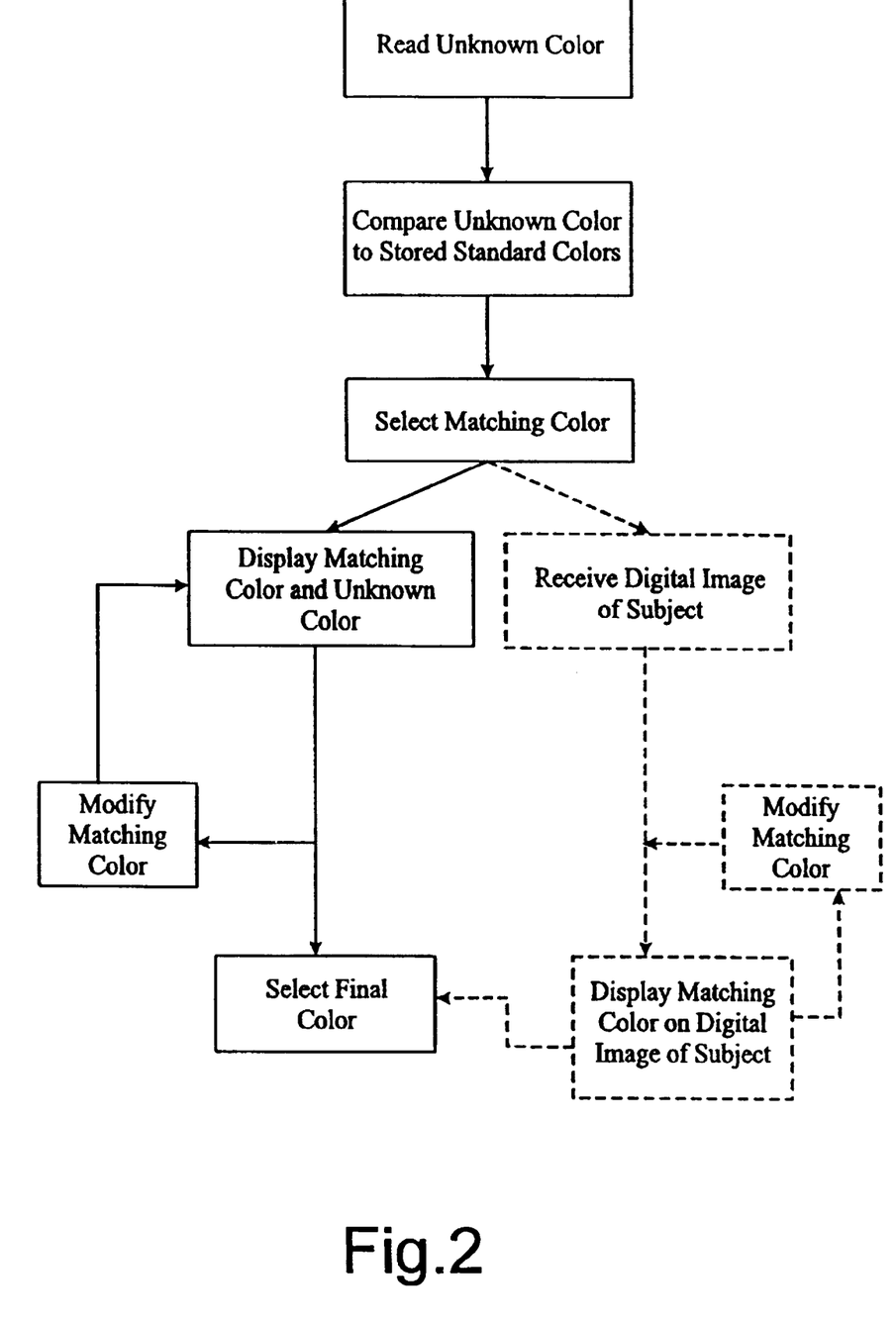
FIG. 2 is a diagram illustrating several embodiments of the color selection portion of the method of the present invention.

In accordance with the invention, the method for creating a customized color cosmetic mass at the point of sale to a customer is illustrated in diagrammatic form in FIGS. 1 and 2. While it should be understood that the present method may be utilized to provide any type of color customized cosmetic mass, such as lipstick, blush, foundation, or any other types of solid color cosmetics, for simplicity, the following description focuses on lipstick. This should not be construed to limit the invention, in any way, to the lipstick art.

The method of the present invention can be generally separated into two phases. A first phase is the color selection phase and a second phase is the mass preparation phase. As illustrated in FIG. 1, the present method first requires selecting a final color. The final color may be selected in any number of different ways. One technique for selecting a final color involves viewing a color chart, such as a standard color pallette, either from a counter display, a computerized display unit, or other display device. In this technique, the customer simply selects one of a number of standard colors. Alternatively, in a similar technique, the customer may select a color in-between two of the standard colors from the pallette, chart, display unit, or the like. Then a computer program having a stored algorithm or similar method of calculation is utilized to identify an appropriate formula for the selected color. In yet another alternative technique, the customer may view an unknown color, such as from a garment or other unknown, and manually select a color from a standard pallette of colors or color chart to manually match the unknown color.

Several other techniques for selecting the final color are illustrated diagrammatically in FIG. 2, with the first technique being shown in solid lines and an alternative technique being shown in part in solid lines and in part in phantom. Referring to FIG. 2, one technique for selecting a final color begins with reading an unknown color. The unknown color may be read from a piece of fabric, a color chart, a customer's skin, a nail color, or any other source. This portion of the process is described in greater detail below. The unknown color is then preferably compared to a standard color pallette, which may be stored in a programmable device such as a computer. After the comparison is completed, a matching color is selected which substantially matches the unknown color. This matching color may be the closest standard color from the color pallette, or, more preferably, may correspond to a color in-between the standard colors which substantially equivalently matches the unknown color. The matching color and unknown color may then be displayed for the customer. This displaying function may take place on a computer screen or other similar display unit. The customer then has the option of selecting the matching color as the final color, or modifying the matching color. If the customer decides to modify the matching color, the newly modified matching color may then, preferably, be redisplayed for the customer to view. The customer may wish to modify the matching color by varying the grade or other color quality. The customer again will have the option to modify the matching color until satisfied with the color selection. When the customer has settled upon a matching color, this final matching color becomes the final color.

Another alternative technique for selecting the final color begins with reading an unknown color, as shown in part in phantom and in part in solid lines in FIG. 2. This unknown color is then preferably compared to a standard color pallette, which may be stored in a programmable device such as a computer. After the comparison is completed, a matching color is selected which substantially matches the unknown color. This matching color may be the closest standard color from the color pallette, or, more preferably, may correspond to an in-between color which substantially equivalently matches the unknown color. The method next includes receiving a digital image of the subject. The digital image may be obtained utilizing a digital camera, which transmits the digital image data to a programmable device which utilizes digital imaging programming to display the digital image. The matching color may then be displayed on the digital image of the subject for the customer to view. This displaying function may occur on a computer screen or other similar display unit. The customer then has the option of selecting the matching color as the final color, or modifying the matching color. If the customer decides to modify the matching color, the newly modified matching color may then, preferably, be redisplayed on the digital image of the subject for the customer to view. The customer again will have the option to modify the matching color until satisfied with the color selection. When the customer has settled upon a matching color, this final matching color becomes the final color.

It should be readily evident to those skilled in the art that variations of this final color selection technique are equally applicable to the present invention. Any combination of the various features can be used singly or in any combination to select a final color.

The final color may be stored in the programmable device for later use by the customer or for use in compiling a database of colors. By storing the final color in the programmable device, the customer can be assured of obtaining the same color cosmetic product at a later date. Customer information, such as name and address, may also be stored in the database, in addition to the final color selection.

While manual selection of colors is contemplated by the present invention, a computerized color analysis and illustration system may be utilized in selecting the final color. A preferred commercially available color analysis program for this purpose is Accu-Find by Colortec. Other color analysis programs are available from such companies as Data Color, X-Rite, Minolta, Schylin, and B.Y.K. Gardiner. The computerized color analysis and illustration system preferably utilizes stored standard colors and is capable of sampling the unknown color through an input device and then searching through the standard colors to find a match.

Input devices, when used, may include colorimeters, spectrophotometers, or the like, and each of the above-noted companies sells this input-type of hardware to accompany their color analysis programs. A colorimeter is a device for measuring color which uses light emitting diodes for the source lighting and sensor array detector technology to detect the reflected light. A spectrophotometer measures color by analyzing the reflected light from an object using a grating (commonly a blazed halographic type). Detectors can be array or single sensor type. Color can be expressed precisely by numerical color notation using L*a*b values. Both colorimeters and spectrophotometers generate information that can be translated by computer programs into L*a*b values.

L*a*b values are a standard measure of the reflectance and color of a sample. The "L" value expresses the amount of lightness or darkness of a color and ranges from 0 (black) to 100 (white). The "a" and "b" values express the actual hue of the color. "a" represents the red to green color range and "b" represents the yellow to blue color range. Pure red is represented by an "a" value of 100 and pure green by an "a" value of −100. Similarly, pure yellow is represented by a "b" value of 100 and pure blue is a "b" value of −100. In this system of notation, the color of a typical red apple might be L=42.8, a=45.0 and b=9.5. More information on the L*a*b color notation system may be obtained from a pamphlet entitled "Precise Color Communication," by Minolta, the disclosure of which is incorporated herein by reference in its entirety.

Although the use of a color analysis program is preferred, the colorimeters or spectrophotometers can alternatively be used in conjunction with a less sophisticated program output, such as an Excel spread sheet, which can be set up with a series of L*a*b values corresponding to the available selection of colors, each of which is matched with a predetermined pellet formula for that color. The input device measures the L*a*b values, and matches them to the L*a*b values on the spread sheet, and the appropriate formula.

The match and the unknown may then be displayed on a calibrated output device, such as a video monitor/printer or LCD panel. An example of commercially available software which may be utilized for illustration and digital image manipulation is PhotoShop 5.0 by Adobe Systems. An Accu-Find Plug-in to PhotoShop 5.0 may be utilized to connect the color selection program to the display program. A PCM Colorimeter by Accuracy Microsystems may be utilized with Accu-Find to make color measurements of the unknown color. Any other commercially available systems may be utilized for performing the same functions described above.

When digital imaging is desired, as described in the alternative embodiment above, additional equipment is utilized to provide picture taking and face image manipulation capability. A digital camera is preferably utilized with image capture software suitable to generate digital image files. An example of a suitable digital camera is the Kodak DC260 or Coolpix 700. A digital imaging manipulation system with software designed to capture a subject's face image is then utilized to manipulate the image with tools designed to enhance the image by adding makeup. The makeup enhancement features may be stored in makeup files and may be used to manipulate the image by using outline tools, brushes, pencils, or any other types of virtual makeup applicators. When digital imaging is desired, a suitable computer, monitor, and printer should be utilized to provide a readily viewable digital image of the subject.

Referring again to FIG. 1, once the final color has been selected, the method includes identifying the appropriate amount of raw product to utilize in the system. The raw product is preferably in the form of individual lipstick color pellets comprised of full formula lipstick masses having standardized colors and pellet weights. Normally, the formula, and therefore the pellets, will be wax-based. However, the pellets can be selected from any material that may be appropriate for a hot-pour type of color cosmetic, for example, non-traditional wax-like materials, including, but not limited to, various fatty alcohols, fatty acids, fatty esters, polyethylenes, polyethylene glycols, and sterols as well as synthetic resinous products having a wax-like, i.e., hard, brittle, relatively non-greasy, texture, such as silicone waxes. Multiple different pellet colors can be provided, and a pellet may be monochromatic or may contain a combination of colors. The colorants which may be used to color the pellets may be any that are routinely used in color cosmetics; these include, but are not limited to metal oxides, for example, red, yellow, black or brown iron oxides or white titanium dioxide; FD&C or D&C organic colors; natural pigments, such as annatto, chlorophyll, carmine and the like; and pearls, such as titanated mica, silica, fish scales, thin flaked alumina, cholesteric or chiral pneumatic liquid crystals. A list of useful colorants for cosmetics can be found, for example, in the International Cosmetic Ingredient Dictionary and Handbook, Volume 2, 7th Edition, 1997 (see pages 1628–30), the disclosure of which is incorporated herein by reference.

In order for each color in the color pallette to be a source of matching, a formula of pellets that will produce that color is predetermined. Determination of the color components needed to reproduce a particular color in a cosmetic is within the ability of an individual of ordinary skill in the color cosmetic art. The formula for each individual color is then coordinated with the color in the pallette. In a preferred embodiment, for example when a color matching and illustration program is used as the source of the standard color pallette, the program permits entry of the individual formulas as part of the program. More preferably, the program is capable of generating intermediate formulas for those colors that are intermediate between the standard pallette colors. In an alternate embodiment, however, the color pallette and pellet formulas may be maintained separately, and can be cross-referenced either manually or via computer.

In a preferred embodiment, the pellets are all of substantially the same weight, most preferably approximately ½ or ¼ gram each, a single lipstick having a total weight of about 5 grams. In an alternative embodiment, the pellets may be different weights or sizes, this element not being critical to the invention. A computer program is preferably utilized to identify the appropriate pellet color and weight combination based upon the final selected color. The combination of pellets is preferably identified from the computer color analysis system, described above in selecting the final color. This program utilizes a standard color pallette file, selects the closest colors from the pallette file and identifies appropriate formulas for matching colors in-between the closest colors from the standard color pallette file utilizing a suitable computer algorithm.

The next step in the method includes positioning the combination of pellets in a container. The container may be any type of container which can withstand the heat necessary to melt the lipstick pellets. A preferred container is compact, plastic, and disposable. The pellets in the container are heated and stirred until the pellets melt to form a mixture. The pellets are heated to a specified temperature which is, preferably, just over the melting point of the wax in the pellets. The temperature will vary depending upon the type of wax used in the base formula. The container may be placed on a heating unit, such as a block heater, to heat the pellets. Again, compactness is important since the present method is to be utilized at the point of sale, which is generally at a cosmetic counter. Thus, a compact heating unit is most preferred. The pellets may be manually stirred using, for instance, a wooden disposable stirrer, in order to create a homogeneous heated mixture.

Once the pellets have been completely melted and stirred to form the homogeneous heated mixture, the mixture is poured into a mold. The mold preferably includes at least one cavity in the shape of a lipstick mass. In one embodiment, two cavities are provided. The mold is preferably of compact size and may be assembled and disassembled manually. After the mixture is poured into the mold, the mold is then associated with a heat transfer apparatus capable of cooling the mold to a set temperature below the lipstick solidification temperature. Any type of cooling apparatus may be utilized. A Peltier cooling plate is one preferable cooling unit because it does not require a compressor. In an alternative embodiment, a single lipstick mass is poured and the remaining mixture is poured into a pan or other appropriate receptacle to form a matching blush.

Once the mixture has cooled to the point of solidification, the mold is removed from the cooling plate and the mass or masses may be removed from the mold by disassembling the mold. Each mass may then be placed in a dispensing unit, such as a lipstick case or compact, for use by the customer.

Figure 3:
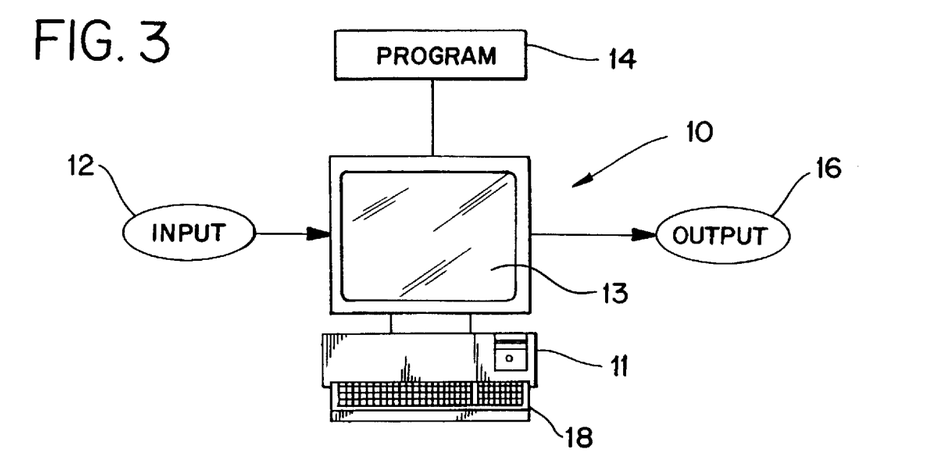
FIG. 3 is a schematic of one embodiment of the programmable device of the present system.

Referring now to FIGS. 3–9, the system of the present invention is illustrated as including a programmable device 10, such as computer 11, a plurality of lipstick pellets 22 having at least two different colors, a container 24, a heating unit 20, a mold 30 and a cooling unit 40. The programmable device 10 is illustrated in FIG. 3. Programmable device 10 receives input 12 and utilizes a computer program 14 to provide output 16. As discussed above, the input 12 may include data concerning an unknown color, a selected color, or a modification of a matching color, among other things. The program 14 may include stored data for a standard color pallette, the color analysis and illustration programming, the digital imaging programming, and the computer algorithm and related programming utilized to identify the appropriate lipstick pellet combination once a final color has been selected, among other things.

Programmable device 10 also preferably includes a keyboard 18, which is used to provide input to the programming 14 of computer 11, and a computer screen 13 for viewing the results of programming 14. In one embodiment of the invention, computer 11 has Windows 95 and a fast video graphics card, with an Intel Pentium II processor having a speed of 300 MHz or faster, and a high quality monitor.

Figure 4:
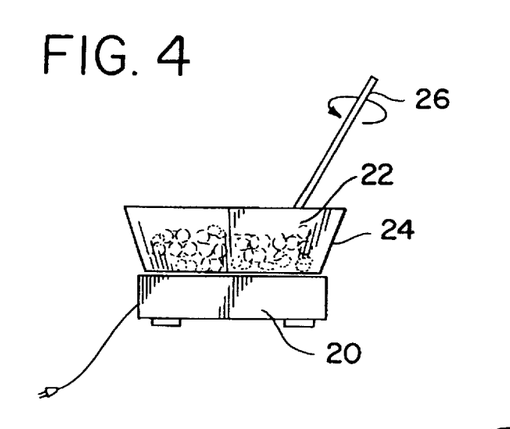
FIG. 4 is a side view of the heating unit of the present system with the lipstick pellets in a heating position.

The system of the present invention also includes a heating unit for heating the pellets in a container. FIG. 4 depicts one embodiment of the heating unit of the present invention as a heating plate 20. A plurality of pellets 22 is placed in a container 24 and container 24 may be seated on the heating plate 20 to melt the pellets 22 in container 24. Container 24 is preferably plastic and disposable, although any type of container may be utilized, as long as it can withstand the heat necessary to melt pellets 22. A stirrer 26, such as a conventional wooden disposable stirrer, may be used to stir the combination of pellets 22 in container 24 during heating. The combination of pellets 22 is preferably heated and stirred until all the pellets have melted and a homogeneous heated mixture is formed. The heating plate 20 should be capable of heating the pellets to a temperature above the melting temperature of the combination of pellets 22 in container 24. It should be noted that any type of heating unit may be utilized, such as a microwave or other type of heating unit. Because the system is utilized behind a cosmetics counter, a smaller heating unit is preferred over a larger unit.

Figure 5:
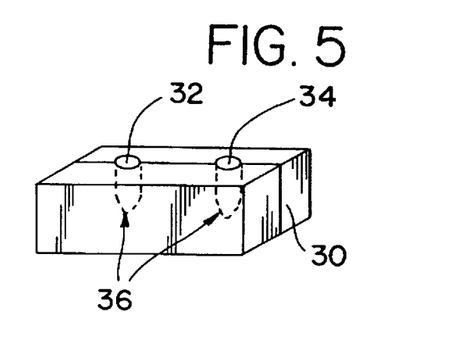
FIG. 5 is an elevated view of the mold of the present system.

The melted mixture may then be poured into a lipstick mold 30, such as that depicted in FIG. 5. The mold 30 has two cavities (32, 34) which are formed in the shape of a lipstick mass 36. The mold 30 is preferably reusable and easily assembled and disassembled. Alternatively, mold 30 may be disposable. Mold 30 is preferably compact in size in order to avoid having to take up a large amount of space behind the counter and to be easily usable with a cooling unit. Two parts of the mold 30 may be provided, as shown in FIG. 5, although the number of parts to the mold is not critical to the invention.

Figures 6, 7, 8:
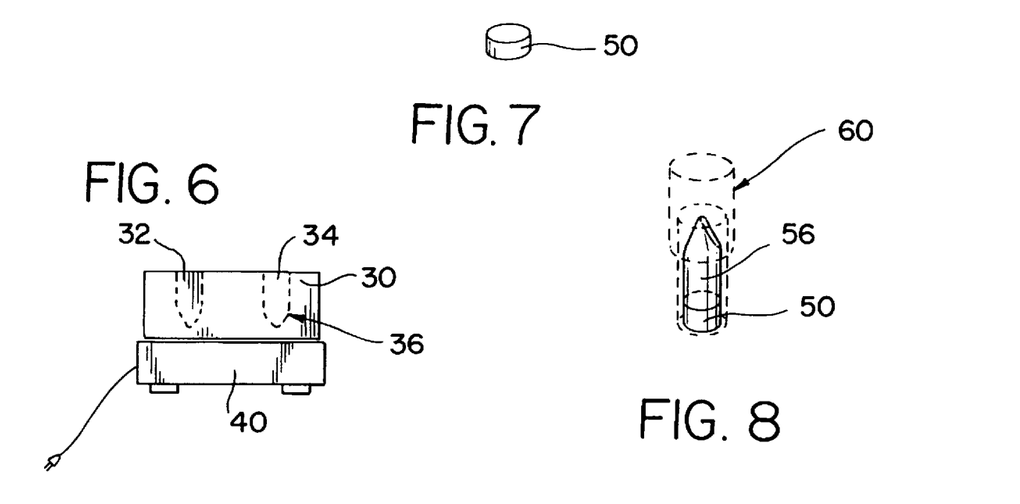
FIG. 6 is a side view of the cooling unit of the present system with the mold in a cooling position.
FIG. 7 is an elevated view of a portion of a dispensing device for use with the present system.
FIG. 8 is an elevated view of the cosmetic mass of the present method and system disposed in a dispensing device, shown in phantom.

After the heated mixture is poured into mold 30, the mold is cooled utilizing a heat transfer apparatus. One embodiment of a heat transfer apparatus is illustrated in FIG. 6 as a cooling plate 40. A Peltier cooling plate is useful for this purpose since it does not require a compressor and is, thus, more compact in size. Cooling plate 40 is preferably capable of cooling the mold 30 so that the heated material solidifies to create formed masses.

After the formed masses solidify, mold 30 is disassembled to release the masses from the mold 30. The masses may be placed in a dispensing unit, such as that shown in FIGS. 7 and 8. For lipstick, the masses can first be placed in a receiving cup. The mass 56 and receiving cup 50 may then be placed in a dispenser 60 (shown in phantom in FIG. 8), such as a conventional lipstick case, and provided to the customer. Any type of dispensing system may be utilized with the masses 56 of the present invention. Dispenser 60, shown in FIG. 8, is provided for illustration purposes only.

Figure 9:
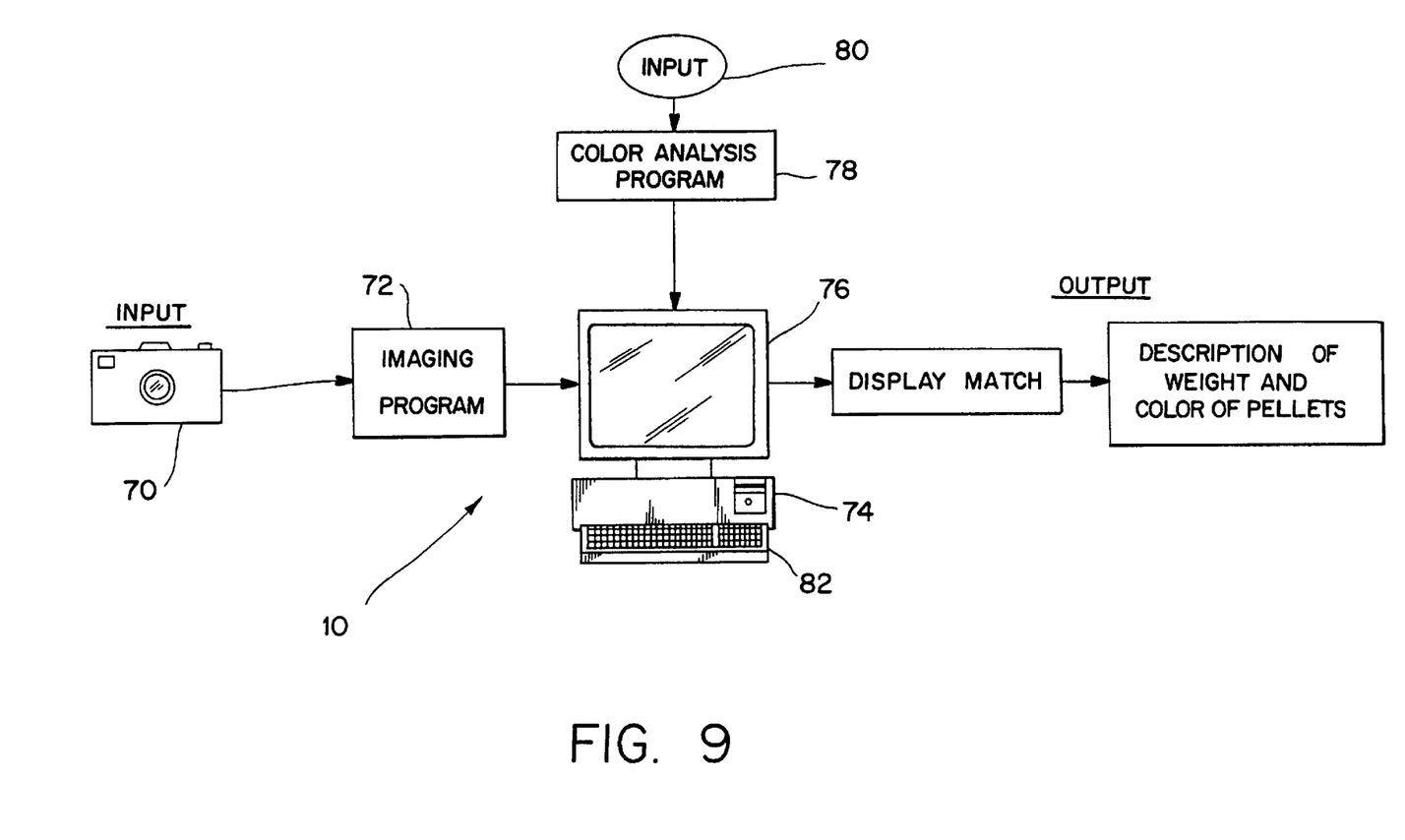
FIG. 9 is a schematic of another embodiment of the programmable device of the present system in combination with a digital imaging device.

Referring to FIG. 9, an alternative embodiment of the programmable device of the present invention is depicted. In this embodiment, a digital imaging device, such as digital camera 70, is utilized to take a digital image of a subject who is preferably the customer. Imaging software 72 is installed in computer 74. Computer 74 receives a digital image from digital camera 70 to create an image on computer screen 76. The computer 74 also includes a color analysis program 78 for analyzing an unknown color, which may be read using an input device 80, and comparing it to a standard color pallette to identify a matching color. Alternatively, a color pallette may be provided on the computer screen and the customer may select a color from the pallette, or may select a color from the pallette with modification.

Programmable device 10 also includes another input device in the form of keyboard 82. Keyboard 82 is utilized to provide input to the imaging program 72 and to the color analysis program 78. For instance, once the customer's image is displayed on computer screen 76 and a matching color is determined, the customer may modify the matching color by varying the shade, grade, or other factor associated with the matching color, to select a more desirable color. Programmable device 10 also includes software for identifying the weight and color combination of lipstick pellets 22 necessary to create the matching color, once the color has been finally selected by the customer.

While various descriptions of the present invention are described above, it should be understood that the various features can be used singly or in any combination thereof. Therefore, this invention is not to be limited to only the specifically preferred embodiments depicted herein. Variations and modifications within the spirit and scope of the invention, beyond those discussed herein, may occur to those skilled in the art to which the invention pertains. For instance, while the present invention is directed toward color customization, the method and system described herein could equally apply to other types of expendable mass products. Accordingly, all expedient modifications readily attainable by one versed in the art from the disclosure set forth herein are to be included as further embodiments of the present invention. The scope of the present invention accordingly is to be defined as set forth in the appended claims.

What is claimed is:

1. A method for creating a customized color cosmetic mass at the point of sale a customer from a plurality of pellets having a plurality of colors comprising:

selecting a final color;

identifying a combination of pellets from the plurality of pellets based upon a pellet weight and the pellet color to create the final color upon combination thereof;

heating the combination of pellets in a container to form a heated material;

transferring the heated material from the container to a mold having at least one opening defining therein a shape of at least one cosmetic mass;

cooling the mold until the heated material solidifies into at least one cosmetic mass; and disassembling the mold to release the at least one cosmetic mass therefrom.

2. The method of claim 1, which further comprises storing said final color in a database.

3. The method of claim 1, wherein the step of selecting a final color comprises: selecting a final color from a standard color pallette.

4. The method of claim 3, wherein the step of selecting a final color further comprises:
modifying said final color from the standard color pallette based up on customer input;
repeating said modifying step until the modified final color is selected as the final color.

5. The method of claim 1, wherein the step of selecting a final color comprises:
reading an unknown color; and
comparing said unknown color to a standard color pallette to select a matching color as said final color.

6. The method of claim 5, wherein the step of selecting a final color further comprises:
displaying said matching color and said unknown color on a display unit.

7. The method of claim 1, wherein the step of selecting a final color comprises:
reading an unknown color;
comparing said unknown color to a standard color pallette to select a matching color;
displaying said matching color and said unknown color on a display unit;
modifying said matching color based upon customer input; and
repeating said displaying and modifying steps until said matching color is selected as said final color.

8. The method of claim 5, wherein the step of selecting a final color further comprises:
receiving a digital image of the customer;
displaying the matching color on said digital image of the customer on a display unit;
modifying said matching color based upon customer input; and
repeating said displaying and modifying steps until said matching color is selected as said final color.

9. The method of claim 1, wherein the step of selecting a final color comprises:
receiving a digital image of the customer; and
displaying the final color on the digital image of the customer on a display unit.

10. The method of claim 1, wherein the step of selecting a final color comprises:
receiving a digital image of the customer;
reading an unknown color;
comparing said unknown color to a standard color pallette to select a matching color;
displaying said matching color and said unknown color on the digital image of the customer;
modifying said matching color based upon customer input; and
repeating said displaying and modifying steps until said matching color is selected as said final color.

11. The method of claim 1, which further comprises positioning the at least one cosmetic mass in a dispensing unit.

12. The method of claim 1, which further comprises stirring said mixture during heating to facilitate the formation of a heated mixture which is homogeneous.

13. A system for providing a customized color cosmetic mass product to a customer at the point of sale, the system comprising:
a plurality of pellets having at least two different colors;
a programmable device for identifying a combination of pellets based upon a weight and a color combination of the plurality of pellets so that when the combination of pellets is formed into a homogeneous mass, said combination of pellets provides a final color for the cosmetic mass;
a container for receiving the combination of pellets;
a heating unit for heating the combination of pellets in the container to form a homogeneous heated mixture;
a mold having at least one mold cavity for defining a shape of the cosmetic mass and for receiving the homogeneous heated mixture; and
a cooling unit for cooling the heated mixture in the mold until the heated mixture solidifies to form the cosmetic mass.

14. The system of claim 13, wherein the cosmetic mass is a lipstick, foundation, or blush.

15. The system of claim 13, wherein the heating unit is a block heater and the cooling unit is a cooling plate and the system further comprises a stirrer for stirring the combination of pellets in the container to create the homogeneous heated mixture.

16. The system of claim 13, wherein the mold is disassemblable to release the at least one cosmetic mass therefrom.

17. The system of claim 13, wherein the programmable device includes a first input unit and is programmed to store a standard color pallette, wherein said first input unit of said programmable device samples an unknown color and said programmable device compares said unknown color to said standard color pallette to identify a matching color.

18. The system of claim 17, wherein said programmable device further comprises a second input device for receiving input from a customer to either select said matching color as the final color or to modify said matching color to provide the final color.

19. The system of claim 13, which further comprises a digital camera for generating a digital image for input to the programmable device, wherein said programmable device is programmed to receive said digital image, to manipulate said digital image, and to display said digital image in combination with said final color.

20. The system of claim 13, wherein said plurality of pellets comprise at least one colorant selected from the group consisting of metal oxides, titanium dioxides, FD&C organic colors, D&C organic colors, natural pigments, and pearls.

* * * * *